US00PP36726P2

(12) United States Plant Patent
Hansen

(10) Patent No.: US PP36,726 P2
(45) Date of Patent: Jun. 3, 2025

(54) ***STOKESIA* PLANT NAMED 'Whitecaps'**

(50) Latin Name: *Stokesia laevis*
Varietal Denomination: Whitecaps

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,958

(22) Filed: Apr. 16, 2024

(51) Int. Cl.
*A01H 5/02* (2018.01)
*A01H 6/14* (2018.01)

(52) U.S. Cl.
USPC ..... Plt./484

(58) Field of Classification Search
USPC ..... Plt./484
See application file for complete search history.

*Primary Examiner* — Susan McCormick Ewoldt
*Assistant Examiner* — Zachariah Allan Kay

(57) ABSTRACT

A new and distinct variety of *Stokesia laevis* plant named 'Whitecaps' with extended blooming of composite flowers having white ray florets and disk florets with a tinge of pale pinkish-lavender displayed just above the rich dark-green foliage of rounded plants from early summer until late summer of into fall if deadheaded. The new plant is useful for garden landscapes, in containers, or as a cut flower.

1 Drawing Sheet

Botanical classification: *Stokesia laevis.*
Variety denomination: 'Whitecaps'.

STATEMENT REGARDING PRIOR DISCLOSURES UNDER 37 CFR 1.77(B)(6)

The sale or offer for sale of the new plant was made by Walters Gardens, Inc. on Apr. 25, 2024, to Pleasant Run Nursery. Walters Gardens, Inc. obtained the new plant and all information about the new plant directly from the inventor. No plants of *Stokesia* 'Whitecaps' have been sold or offered for sale in this country or anywhere in the world nor has any disclosure of the new plant been made more than one year prior to the filing date of this application, and such sale or disclosure within one year was either derived directly or indirectly from the inventor.

BACKGROUND AND ORIGIN OF THE PLANT

The present invention relates to the new and distinct plant, *Stokesia laevis* 'Whitecaps', hereinafter also referred to as 'Whitecaps', and the new plant as a new and unique selection of Stokes' Aster. The new plant is useful in the ornamental landscape as an accent, en masse, or in a container.

'Whitecaps' was hybridized under the direction of a professor at North Carolina State University prior to the summer of 2011 and sown at a wholesale perennial nursery in Zeeland, Michigan in late winter of 2018. The new plant was selected by the inventor as a single seedling from a cross made between a proprietary seedling with maroon flowers assigned the name 'Maroon' (not patented) as the female parent and 'Peachie's Pick' (not patented) as the male parent at a wholesale perennial nursery in Zeeland, Michigan. The new plant was originally selected from full-sun trials in the summer of 2019 at a wholesale perennial nursery in Zeeland, Michigan. While in the trials, the new plant was assigned the breeder code 18-30-2. Asexual propagation of the new variety by division since in the fall of 2019 at the same nursery and later by sterile shoot tip tissue culture has demonstrated that the new plant maintains its unique characteristics and is capable of reproducing identical individuals in successive generations.

SUMMARY OF THE INVENTION

'Whitecaps' differs from all other Stoke's Aster known to the applicant. The nearest known cultivars are: 'Alba' (not patented), 'Divinity' U.S. Plant Pat. No. 26,164, 'Silver Moon' (not patented), 'White Star' (not patented), and 'White Surprise' (not patented).

'Alba' has a smaller habit and the flowers are more white. 'Divinity' has more compact habit and white flowers with a light blush of yellow. 'Silver Moon' has a smaller habit with smaller flowers that that have fewer ray florets. 'White Star' has a more compact habit. 'White Surprise' is more compact in habit and has fewer ray florets per inflorescence.

The female parent has burgundy-maroon flowers with a more open habit and fewer flowers. The male parent has flowers that are lavender blue with a slightly smaller habit.

*Stokesia* 'Whitecaps' has several unique characteristics that have been observed. The combination of these traits makes 'Whitecaps' distinct from the parent plants and all other Stokes' Aster cultivars known to the inventor.

The following unique characteristics, in combination, distinguish 'Whitecaps' as a new and distinct variety of Stokes' Aster:

1. Compact rounded habit flowering just above the rich dark-green foliage;
2. Large composite flowers of near white ray florets with a pale pinkish-lavender tinge;
3. Long flowering season from early to late summer or early fall if deadheaded;
4. Stems upright and strongly branching.

BRIEF DESCRIPTION OF THE DRAWINGS

The accompanying color photographic drawings illustrate the distinct characteristics of a new two-year-old plant to the extent reasonably possible through color reproductions.

DETAILED BOTANICAL DESCRIPTION OF THE INVENTION

Figure 1:
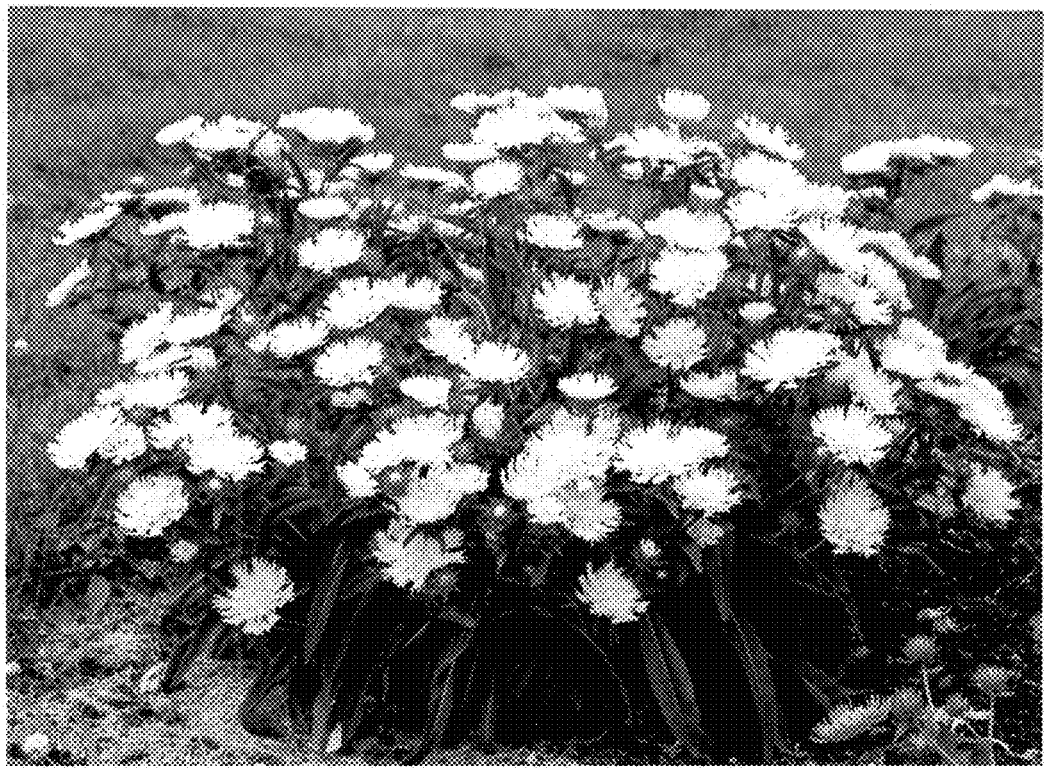
FIG. 1 shows the overall plant in a landscape in full flower.
Figure 2:
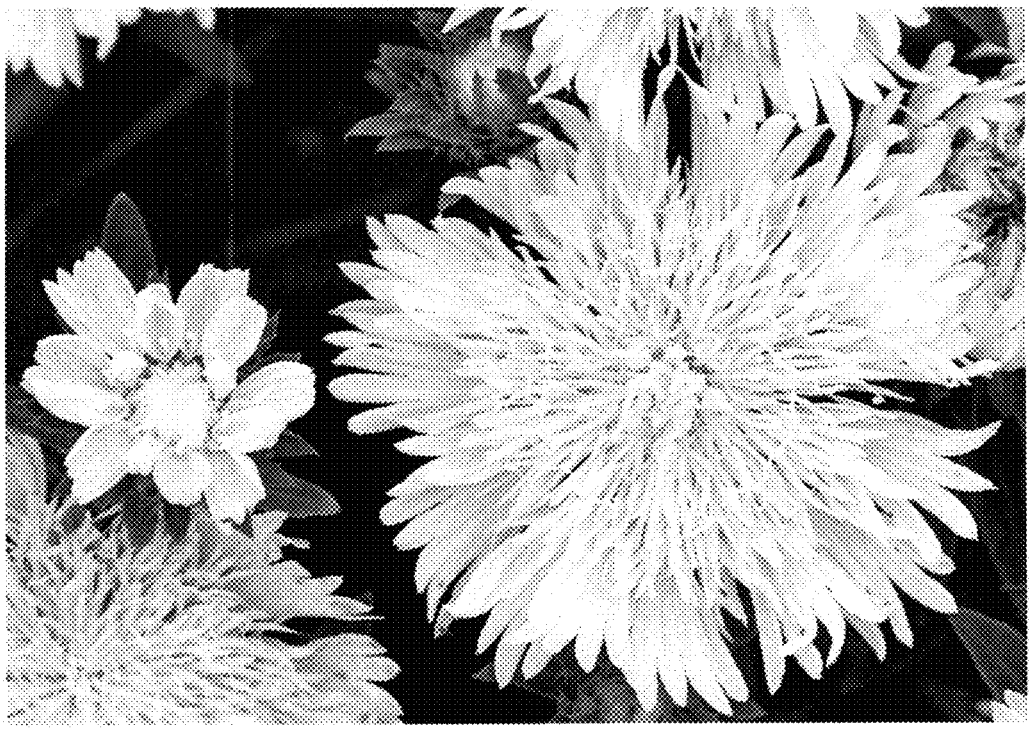
FIG. 2 shows a close-up from above of some inflorescences at different stages.

The new plant has not been tested in every possible environmental condition. The phenotype may vary slightly with different growing conditions, such as light intensity, temperature, fertility, and water availability, without, however, any variation in the genotype.

The new plant being described is a two-year-old plant growing in a full-sun display garden in Zeeland, Michigan in sandy loam soil. All color descriptions are based on the 2015 copyright edition of The Royal Horticultural Colour Chart and accompanying designation, except where general dictionary terms are used.

Plant habit: Herbaceous perennial, rounded mound with numerous stiffly upright leaves, especially when young; about 28 inflorescence stems per plant;

Plant size: Flowering to about 62 cm wide and 50 cm tall; branched inflorescences to about 45 cm tall;

Root: Dense, thick, fibrous; color variable depending on soil matrix, typically, between RHS 158D and RHS 164D;

Stem: About 28 per plant; stiff; upright; cylindrical; branched; lanulose; to about 48 cm long and 8 mm diameter at base; with typically six cauline leaves; average internode distance about 3.8 cm;

Stem color: Between RHS 191B and RHS 138B;

Parentage: Female or seed parent is 'Maroon', male or pollen parent is 'Peachie's Pick';

Foliage: Lanceolate; acute apex; cuneate base; margin entire; glabrous and matte adaxial and abaxial;

Foliage size: To about 22 cm long and 3.5 cm wide;

Leaf color: Young adaxial between RHS 138A and RHS 146A, abaxial nearest RHS 146B; mature adaxial nearest RHS 137B, abaxial between RHS 147B and RHS 147C;

Veins: Pinnate; glabrous adaxial and abaxial;

Vein color: Adaxial midrib and secondary veins nearest RHS 145D; abaxial proximal midrib nearest RHS 145D, distal midrib nearest RHS 146D and secondary veins not prominent;

Cauline leaves: Six; lanceolate; acute apex, partially clasping base; margin entire or with five to eight apiculate teeth about 2 mm long in the basal 10 mm; color same as basal leaves;

Petiole: Slightly concavo-convex; glabrous adaxial and abaxial; size to about 14.3 cm long and 10 mm wide at flared;

Petiole color: Adaxial and abaxial edge nearest RHS 137B; adaxial center between RHS 154C and RHS 145D, adaxial base between RHS 186B and RHS 186C; abaxial center nearest RHS 145D;

Inflorescence: Capitulum; four to thirteen per stem; with about 20 to 24 ray florets and about 120 to 150 disk florets; to about 10 cm wide and 4 cm tall;

Peduncle: Branched, erect, corymb, branches 3 to 15 cm long on stems to 48 cm tall, 2 to 3 mm diameter at the base; 28 per plant with initial flowering, to about 70 per plant per season;

Peduncle color: Between RHS 191B and RHS 138B;

Flower period: Early summer through late summer, extending into early fall if deadheaded;

Inflorescences per plant: 140 to 175 during the main period, 250 to 400 per season;

Lasting: About 2 weeks on plant, 1.5 weeks as cut;

Inflorescence bud size: With ray florets upright to about 2 cm diameter and 2.5 cm tall;

Inflorescence bud color: Exposed petals three to five days before petals are horizontal between RHS 76C and RHS 76D; phyllaries adaxial nearest RHS 137A and abaxial between RHS 138A and RHS 138B;

Ray florets: 20 to 24 per flower; sterile; with single whorl around the exterior of inflorescence;

ligule distally deeply cleft into about 5 lobes, with acute apices; basal 13 mm tubular; to 35 mm long, to 19 mm wide at apex, 3 to 5 mm wide at the base, lobes 10 to 15 mm long and 2mm to 3 mm wide;

Ray floret color: When first opening adaxial and abaxial nearest RHS NN155C distally and nearest RHS NN155A in corolla tube; in mid-maturity adaxial and abaxial distal portion nearest RHS NN155A with a light blush nearest to RHS 76D, corolla tube adaxial and abaxial nearest RHS NN155B; at full maturity before withering, adaxial and abaxial distal portion nearest RHS NN155A with a moderate blush of RHS 76D, corolla tube remains nearest RHS NN155B;

Disk florets: 120 to 150 per inflorescence; perfect; five or six lobed with apices acute and margin entire; corolla to 23 mm long, and flaring to about 20 mm wide; corolla tube about 13 mm long, 2 mm diameter just below fusion point and base about 1 mm diameter; individual lobes to about 10 mm long and 1.5 mm wide;

Disk corolla color: When first opening adaxial and abaxial nearest RHS NN155C distally and nearest RHS NN155A in corolla tube; in mid-maturity adaxial and abaxial distal portion nearest RHS NN155A with a light blush of nearest RHS 76D, corolla tube adaxial and abaxial nearest RHS NN155B; at full maturity before withering, adaxial and abaxial distal portion nearest RHS NN155A with a moderate blush of RHS 76D, corolla tube remains nearest RHS NN155B;

Androecium: Adnate to inner corolla; connate;

*Filaments*.—Five; adnate to inner corolla in proximal 10 mm, free in distal 2 mm; to 2 mm long and about 0.2 mm diameter; color in adnate portion nearest RHS 155D, free portion nearest RHS NN155C.

*Anther*.—Connate, fully surrounding style; 3 mm long and fused to about 0.7 mm diameter; color nearest RHS 155A.

*Pollen*.—Abundant; color nearest RHS 19B.

Gynoecium: Single; to about 25 mm long;

*Style*.—Straight; to 18 mm long and 0.2 mm diameter; color nearest RHS NN155C.

*Stigma*.—Bifid; reflexed 180°; to about 5 mm long and 0.2 mm diameter; color nearest RHS NN155B.

*Ovary*.—About 1 mm long; color nearest RHS 155C.

Involucre: Arranged in two sets below inflorescence; lower or outer set with about 28 lanceolate phyllaries in two to three whorls; acute to apiculate apex; truncate base; margin dentate with 9 to 10 teeth with apiculate to bi-apiculate apices from 2.5 mm to 5 mm long; overall size to 45 mm long and 16 mm across including teeth decreasing distally, color adaxial RHS 137A abaxial RHS 138A; upper or inner set with about 22 lanceolate phyllaries in about three whorls; acute and ciliolate apex; truncate base; margin entire; to about 17 mm long and 3.5 mm across, decreasing in size distally; adaxial and abaxial margin translucent to nearest RHS 155B, adaxial and abaxial center nearest RHS 144A;

Seeds: About 120 to 150 per flower; angular; from about 4.5 mm to 6 mm long by 1 mm to 3 mm wide; color nearest RHS 199A when mature;

Rooted tissue culture plugs finish to flower in 10 to 12 weeks in 3.8-liter containers;

Plant vigor and growth rate are moderate to good.

The plant does not show any pest or disease resistance or susceptibility other than what is normal. for *Stokesia.*

I claim:

1. A new and distinct *Stokesia laevis* plant named 'Whitecaps' as herein described and illustrated.

* * * * *